United States Patent [19]

Messing

[11] 3,930,951
[45] Jan. 6, 1976

[54] BONDING ENZYMES TO POROUS INORGANIC CARRIERS
[75] Inventor: Ralph A. Messing, Horseheads, N.Y.
[73] Assignee: Corning Glass Works, Corning, N.Y.
[22] Filed: May 28, 1974
[21] Appl. No.: 473,717

[52] U.S. Cl. ............... 195/63; 195/68; 195/DIG. 11
[51] Int. Cl.² ............................................ C07G 7/02
[58] Field of Search ................ 195/63, 68, DIG. 11; 252/466

[56] References Cited
UNITED STATES PATENTS

| | | | |
|---|---|---|---|
| 2,968,635 | 1/1961 | Nixon | 252/466 |
| 3,666,627 | 5/1972 | Messing | 195/68 |
| 3,669,841 | 6/1972 | Miller | 195/63 |
| 3,705,084 | 12/1972 | Reynolds | 195/63 |
| 3,783,101 | 1/1974 | Tomb et al. | 195/63 |
| 3,804,719 | 4/1974 | Messing | 195/68 |

OTHER PUBLICATIONS
Zaborsky, O., *Immobilized Enzymes*, The Chemical Rubber Co., Cleveland, Ohio, 1973. (pp. 61, 62, 70, 72 & 73).

*Primary Examiner*—David M. Naff
*Attorney, Agent, or Firm*—James A. Giblin; Clinton S. Janes, Jr.; Clarence R. Patty, Jr.

[57] ABSTRACT

Enzymes can be coupled chemically to various water-insoluble inorganic carriers by reacting the carriers with 4,4'-bi(methoxybenzenediazonium chloride) to form a surface of diazo groups which are subsequently reacted with an enzyme solution to immobilize the enzymes. In preferred embodiments, the inorganic carriers are highly porous, have an average pore size of less than about 1000 A, and consist of 4–200 mesh porous particles of materials selected from the group consisting of glass, silica, alumina, and mixtures of silica and alumina.

6 Claims, No Drawings

BONDING ENZYMES TO POROUS INORGANIC CARRIERS

BACKGROUND

1. Field

This invention is concerned generally with the immobilization of enzymes onto water-insoluble carrier materials and specifically with the covalent bonding of enzymes to high surface area, porous inorganic support materials in such a manner that the immobilized enzymes demonstrate retention of enzymatic activity and stability.

2. Prior Art

The desirability of fixing active enzymes on essentially water-insoluble support materials to form readily removable and reusable composites is well recognized. Since enzymes are highly specific in promoting certain chemical reactions, their use, especially in immobilized and hence, reusable form, has very practical appeal in laboratory and industrial applications.

Enzymes have been attached by a variety of methods to numerous water-insoluble support materials, both organic and, more recently, inorganic materials. Methods for immobilizing enzymes on various inorganic materials are described in U.S. Pat. No. 3,556,945 (adsorption on siliceous materials). In U.S. Pat. No. 3,519,538, there are disclosed methods for covalently bonding enzymes to numerous inorganic carriers via intermediate silane coupling agents. Methods of bonding enzymes to porous inorganic carriers having an average pore diameter range which maximizes enzyme loading and half life are described in patent applications Ser. No. 332,807, now U.S. Pat. No. 3,850,751, and Ser. No. 332,804, now U.S. Pat. No. 3,841,971, respectively entitled "Enzymes Immobilized on Porous Inorganic Support Materials" and "Synergistic Enzymes Adsorbed Within Porous Inorganic Carriers". Both of the above applications were filed on Feb. 16, 1973 in the name of R. A. Messing and are assigned to the present assignee. In U.S. patent application Ser. No. 454,140, filed on Mar. 25, 1974, in the name of R. A. Messing, entitled "Method of Immobilizing Urease on Porous Titania", and assigned to the present assignee, methods of pretreating porous titania with stannous ions to maximize loading and half-life of the urease are disclosed.

Although the above disclosures show both the adsorption and chemical coupling of enzymes to inorganic support materials, it can be appreciated that there exist various advantages and disadvantages with each system. For example, as a general rule, adsorbed enzyme systems are relatively inexpensive to prepare and use. On the other hand, adsorbed enzymes are fixed to the carrier by relatively weak bonds and, hence, can detach relatively easy. One method for minimizing such detachment, as shown in Ser. No. 332,807, involves using porous inorganic carriers having an average pore diameter which is very small, e.g., less than 1000 A, very preferably, less than about 500 A.

In the case of enzymes coupled chemically to inorganic carriers via covalent bonds (e.g. U.S. Pat. No. 3,519,538, disclosing the use of an intermediate silane coupling agent), the enzymes are fixed to the surface relatively firmly. On the other hand, such chemically coupled enzyme systems are relatively time consuming and expensive to prepare and use.

I have now prepared an immobilized enzyme system using inorganic carriers which has many of the advantages of past systems with minimal disadvantages in that the enzymes are chemically coupled to the inorganic carrier but in a relatively simple and economical manner. The immobilized enzyme composites and methods for preparing them are described in detail below.

SUMMARY OF THE INVENTION

My method of preparing immobilized enzyme composites comprises the steps of reacting a high surface area, porous, essentially water-insoluble inorganic carrier material with a solution of 4,4'-bi (2-methoxybenzenediazonium chloride), or BMBD, to form on the inorganic surface active diazo groups and then reacting the treated carrier with an aqueous enzyme solution to chemically couple the enzyme through the BMBD residue to the carrier. In preferred embodiments, the inorganic carrier material consists of porous inorganic particles having an average pore diameter at least as large as the larger of the enzyme or its substrate but less than about 1000 A, and a mesh size between about 4 and 200 mesh, U.S. Standard Sieve, the individual particles consisting of either porous glass or agglomerated metal oxide particles selected from the group consisting of $SiO_2$, $Al_2O_3$, and mixtures thereof.

SPECIFIC EMBODIMENTS

The carriers found useful for preparing the composites are known and described, for example, in Ser. No. 332,807, cited above. Very broadly porous $SiO_2$, porous $Al_2O_3$, or mixtures thereof having an average pore diameter of less than about 1000 A, preferably less than about 500 A, can be made by agglomerating the respective metal oxide particles having an average particle size about equal to the desired average pore diameter and then firing the agglomerated particles to a temperature range of about 500°C to about 600°C for about 1 to 3 hours. Illustrative examples for forming such porous bodies can be found in co-pending patent application Ser. No. 344,964, entitled "Method of Making Porous Inorganic Bodies", filed on Mar. 26, 1973 in the name of R. A. Messing and assigned to the present assignee. It should be stressed, however, that such porous bodies can be formed by other methods known in the art. For example a xerogel consisting of metal oxide particles of less than 1000 A particle size can be formed and then dried to remove water and fired to a temperature just below sintering temperature for a few hours.

Porous glass is well known and commercially available. Examples of how to form porous glass can be found, for example, in U.S. Pat. No. 2,106,744, U.S. Pat. No. 2,315,329, and U.S. Pat. No. 3,549,524.

For some industrial applications, it is desirable to use immobilized enzyme composites which include a carrier in particulate form, especially for continuous flow-through enzymatic processes. As pointed out in Ser. No. 332,807, for such operations, a preferred average particle size of the porous inorganic carriers is between about 4 and 200 mesh, U.S. Standard Sieve, preferably between about 25 and 80 mesh. The particles should be at least larger than 200 mesh to facilitate handling and to avoid large pressure drops in, for example, flow-through columns. The particle size should not exceed about 4 mesh to assure adequate diffusion of coupling agent, enzymes, and substrate through the particles to utilize the largely internal surface area which is preferably at least 5 m²/g. Various porous particle mesh sizes within the above ranges can be achieved by conventional spray drying and/or milling and sorting techniques.

As disclosed in Ser. No. 332,807, a very efficient immobilized enzyme composite results when the average pore size of the porous inorganic carrier is less than about 1000 A and preferably less than about 500 A. Ideally, the average pore size of a given inorganic carrier is related to the anticipated enzyme and/or substrate size. For example, if an enzyme substrate is considerably smaller than the enzyme itself, the average carrier pore size need only be at least as large as the enzyme size and less than about 1000 A. However, if the substrate is larger than the enzyme, as in the case of various proteins upon which certain relatively small protease enzymes act, then the average pore size should be at least large enough to permit diffusion of the substrate within the pores to the internally attached enzymes. The upper limit of an average pore diameter of about 1000 A is determined by at least two factors. Firstly, to assure a minimum surface area of at least about 5 m²/g, the average pore size should not exceed about 1000 A. Secondly, by limiting the pore size to about 1000 A, the immobilized enzymes are afforded some degree of protection from detachment, especially in a flow-through pressurized environment, since the small and rigid pores minimize the effect of turbulent forces against an enzyme fixed within the small pores.

In the examples below, the average pore sizes of the carriers were, in most cases, directly related to the size of the anticipated enzyme to be immobilized within the pores or the size of the anticipated substrate, whichever was larger. For example, in the cases of immobilized papain (48 A) and immobilized alkaline *Bacillus subtilis* protease (42 A), the average pore sizes of the carriers were such that they would permit internal diffusion of the somewhat larger substrate, casein (about 100 A), e.g. about 550 A average pore diameter. In the case of immobilized glucose isomerase (about 75–100 A), however, which acts on the relatively small glucose molecule to isomerize it to fructose, an average pore size of 270 A was found useful. As a general rule, I have found that the average pore size of a carrier should be as small as possible, at least as large as the enzyme and/or its substrate, whichever is larger and between about 100 A and 1000 A.

As shown in the examples, the porous inorganic carrier need not consist of only one metal oxide. Mixed metal oxide carriers (e.g., $SiO_2$-$Al_2O_3$) can be readily prepared by simply agglomerating mixtures of metal oxide particles having an average particle size approximately, or averaging, the desired average pore size.

In the examples below, the various immobilized enzyme composites were prepared by reacting a solution of the BMBD with the individual amounts of porous carrier to form a carrier surface of available diazo groups. The treated carriers are then reacted with the enzyme solutions to couple, via azo-linkages, the enzymes to the carriers. The enzymes need only have functional groups capable of reacting with the available surface azo groups (e.g. available -$NH_2$ or tyrosine residue groups on the enzyme molecules).

By choosing BMBD as the bifunctional diazonium salt, the residue of which acts as an intermediate coupling agent, a relatively broad range of solvents are available and a simple immobilization procedure is provided. Further, by avoiding such other bifunctional compounds as tetrazotized benzidine, it is thought that a relatively safe compound can be used in the coupling procedure since, to date, BMBD is considered relatively safe to use in most laboratories (cf. tetrazotized benzidine).

The reaction of the BMBD solution with the essentially water-insoluble inorganic carriers is thought to take place through available surface hydroxyl groups of the respective carriers according to the following illustrative reaction where silica or porous glass is used as the carrier:

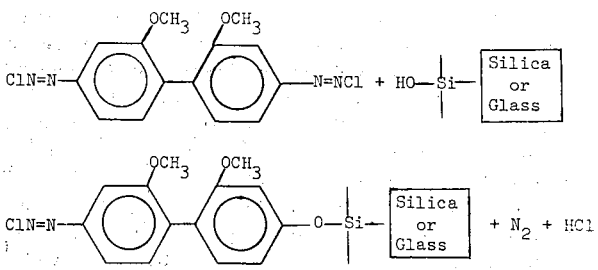

After the BMBD reacts with the inorganic surface, the remaining ClN=N - group of the BMBD residue is available for subsequent reaction with reactive sites on the enzyme molecules.

In the following examples, the various reactants and reaction conditions are described in detail. In Example I, a control composite was prepared by using the same enzyme and carrier and adsorbing the enzyme to the internal surface of the carriers. The control composites provided a basis for comparing the overall utility of the coupling method in which the BMBD was used. Unless otherwise indicated, all composites were assayed for enzymatic activity using standard reagents and conventional assay techniques.

EXAMPLE I

Alkaline Bacillus Subtilis Protease Coupled to Porous Silica

In this example, the porous inorganic carrier consisted of 60–100 mesh porous $SiO_2$ particles having a surface area of about 50 m²/g, a pore volume of 0.8 cc/g and an average pore diameter of about 510 A with a maximum pore size of 680 A and a minimum pore size of 350 A.

The solution of 4,4'-bi(2 methoxybenzenediazonium chloride) was a 0.01% aqueous solution prepared by transferring 1 mg of the BMBD salt to a 10 ml cylinder, diluting to the 10 ml mark with distilled water and then sonicating the slurry at room temperature in an ultrasonic bath until the salt was dissolved (about 5 minutes).

The alkaline *Bacillus subtilis* protease was that supplied under the trade name Alcalase by Novo Industries. Two examples each of composites prepared by adsorption and coupling with the BMBD were prepared and compared as to enzyme activity over the same period of time. All four samples were prepared essentially simultaneously and assayed simultaneously over the same time span. The average activities of the two samples in each set at each indicated time period are shown below.

The immobilized enzyme composites were assayed with a 1% casein solution in 0.1 M phosphate buffer, pH 7.8, at 37°C in a shaking water bath. The results of these assays were compared to a standard curve produced by relating the optical density at 280 millimicrons of a trichloroacetic acid extract of the reaction mixture to the number of milligrams of free enzyme utilized in the assay. From this, one could obtain the number of mg of active enzyme remaining on the carrier over various periods of time.

Immobilization by Adsorption: To each of two 500 mg of 60-100 mesh porous silica samples in separate 25 ml Erlenmeyer flasks, 9 ml of 0.5 M sodium bicarbonate was added. The flasks were placed in a shaking water bath at 37°C and shaken for 1½ hours. The sodium bicarbonate was decanted and the porous bodies were washed with water. After decanting the water wash, 10 ml of enzyme solution containing 2 grams of the Alcalase in 0.10 M phosphate buffer pH 7.8 was added to each sample of porous bodies. The flasks containing the carrier and the enzyme suspension were placed in the 37°C shaking bath and shaken for 3 hours. The samples were then removed from the bath and allowed to stand at room temperature overnight. The enzyme solutions were then decanted from the porous bodies and the immobilized enzyme was washed first with water and then with 0.5 M sodium chloride and finally again rewashed with water. The samples were stored in water at room temperature between assays for the half-life determination period.

Immobilization by Direct Coupling via BMBD Residue: To each of two 500 mg samples of 60-100 mesh porous silica samples separate 25 ml Erlenmeyer flasks were added 2 ml of the 0.01%, diazonium coupling solution and the coupling solution was allowed to react at room temperature with occasional shaking. The porous silica bodies turned red during this period of time. At the end of 20 minutes the coupling solution was decanted and the porous bodies were washed with distilled water. The distilled water was then decanted and 10 ml of enzyme solution containing 2 gms of the Alcalase$^{TM}$ in 0.1 M phosphate buffer pH 7.8 was added to each of the flasks containing the 500 mg sample of pretreated porous silica. The flasks containing the enzyme and carrier were placed in a shaking water bath at 37°C and reacted with shaking at this temperature for 3 hours. The flasks were then removed from the bath and allowed to stand at room temperature overnight. The samples were then washed with water followed by 0.5 M sodium chloride and finally with water. The samples were stored in water at room temperature between assays over the half-life determination period.

All four composites were assayed over a period of 103 days to determine the amounts of active enzyme calculated to mg of active enzyme per gram of carrier for each composite. The average of activity determinations for each set of composites is shown in Table I.

TABLE I

| Days | mg of Active Protease/gram Carrier | |
|---|---|---|
| | Adsorbed | Coupled |
| 3 | 7.20 | 7.52 |
| 6 | 7.28 | 6.96 |
| 14 | 6.64 | 6.72 |
| 26 | 5.52 | 6.44 |
| 45 | 3.92 | 5.60 |
| 70 | 2.48 | 3.92 |
| 82 | 2.20 | 3.84 |
| 95 | 2.28 | 3.80 |
| 103 | 1.84 | 3.08 |

As can be seen from the above table, the half life activity of the adsorbed enzyme is about 3.60 mg/g and that activity level is achieved some time between 45 and 70 days; by plotting the results on a curve, the half-life appeared to be about 48 days. The half life activity of the coupled enzyme is 3.76 mg/g, achieved some where between 95 and 103 days; by plotting, at about 83 days. Thus, the enzymatic half life of the coupled enzyme is about twice that of the adsorbed enzyme.

EXAMPLE II

Papain Coupled to Porous Glass Particles

In this example, the inorganic carrier consisted of porous glass particles of about 60 to 80 mesh having an average pore diameter of about 550 A. The BMBD solution consisted of 10 mg BMBD dissolved in 10 ml of dimethylsulfoxide. The papain solution consisted of 200 mg of crude papain (Nutritional Biochemical Co.) dissolved in 10 ml of an aqueous, 0.2 M $NaHCO_3$, pH 8.1.

To 100 mg of the porous glass particles, 0.5 ml of the BMBD solution was added and allowed to stand at room temperature for 1¾ hours. The residual BMBD solution was then decanted and the treated carrier (in a 10 ml cylinder) was placed in a 5°C water bath. Two ml of 0.2 M $KH_2PO_4$ solution was added and the cylinder was shaken in a reciprocal 5°C shaking bath for 15 minutes. The $KH_2PO_4$ solution was then decanted and a fresh 4 ml of 0.2 M $KH_2PO_4$ was added to extract at room temperature for 15 minutes. The $KH_2PO_4$ solution was decanted and the cylinder again placed in a 5°C bath.

Then 2 ml of the papain solution containing 40 mg of papain preparation was added to the treated carrier and the cylinder was reciprocally shaken for 3 hours and 50 minutes in the 5°C bath. The shaking was then stopped and the reaction allowed to continue at 5°C overnight. About 13 hours later, the shaking was continued for about 20 minutes and the enzyme solution was then decanted. Ten ml $H_2O$ were added to the cylinder, mixed, and the contents were allowed to stand for 10 minutes. This water wash was repeated two more times. The final wash was decanted and 3 ml of a solution containing 0.01 M cysteine and 0.002 molar E.D.T.A. buffered to pH 5.8 with 0.2 M phosphate buffer was added. The immobilized papain sample was repetitively assayed with casein in the presence of cysteine and E.D.T.A. with storage in water at room temperature between assays The assay results are shown in Table II wherein the mg activity of active papain is expressed as mg active papain/gram (e.g. results using 100 mg of carrier multiplied by 10).

TABLE II

| Day | mg Active Papain/Gram Carrier mg Active Papain/g |
|---|---|
| 1 (A.M.) | 39.0 |
| 1 (P.M.) | 35.6 |
| 2 | 28.2 |
| 7 | 19.2 |
| 21 | 21.4 |
| 34 | 14.8 |
| 49 | 11.4 |
| 63 | 7.8 |

EXAMPLE III

Papain Coupled to Porous Glass Particles

In this example the BMBD solution was prepared by dissolving 10 mg of BMBD in 10 ml of a 5% $NH_4HCO_3$ solution. The porous glass particles were similar to those used in Example II. The papain solution was prepared by mixing 250 mg of the crude papain in a 5 ml aqueous solution containing 0.01 M cysteine and 0.002 Molar E.D.T.A. buffered to pH 5.8 with 0.2 M phosphate buffer.

One ml of the BMBD solution was added to 100 mg of the porous glass particles in a 10 ml cylinder placed in a 5°C bath and then allowed to react overnight. The cylinder was removed from the bath and the contents were transferred to a fritted glass (course) funnel by washing the particles out of the cylinder with a 5% $NH_4HCO_3$ solution and washed with distilled water. The washed glass derivative was then transferred to a clean cylinder placed in a 5°C bath to cool.

Two ml of the papain solution (containing 100 mg crude papain) was added to the treated glass, mixed, and allowed to react, without shaking, in the 5°C bath for 15 minutes. Then the mixture was reciprocally shaken in the bath for 8½ hours, the shaking stopped, and the reaction allowed to continue over the weekend at 5°C. Then the shaking was commenced for about 5 minutes, stopped, and the unreacted papain solution decanted. Ten ml of distilled water was added to the composite which was then shaken in the 5°C bath for 20 minutes. The water was decanted and the washing and shaking procedure repeated. The water was again decanted and the composite was transferred to a 25 ml flask to which was added 4 ml of a solution containing 0.01 M cysteine and 0.002 molar E.D.T.A., buffered to pH 5.8 with 0.2 M phosphate buffer. The flask was placed in a 40°C shaking bath and shaken for 20 minutes, after which the solution was decanted and the immobilized enzyme composite was assayed. The repetitive assays were with casein in the presence of cysteine and E.D.T.A. with storage in water at room temperature between assays. The results, calculated to mg active papain per gram of composite, are shown in Table III.

TABLE III

| Assay Day | mg Active Papain/gram |
|---|---|
| 1 A.M. | 66.0 |
| 1 Midday | 52.4 |
| 1 P.M. | 52.4 |
| 2 | 36.0 |
| 16 | 35.4 |
| 29 | 26.0 |
| 44 | 20.2 |
| 58 | 14.6 |

EXAMPLE IV

Glucose Isomerase Coupled to Porous $SiO_2$-$Al_2O_3$

In this example, the porous inorganic carrier consisted of 25–60 mesh particles of a porous $SiO_2$-$Al_2O_3$ composition. The porous particles consisted of agglomerated $SiO_2$ (500 A) and $Al_2O_3$ (167 A) particles in which the amount of $SiO_2$ was about 50% by weight. The average pore diameter was about 270 A with a minimum pore diameter of 190 A and a maximum pore diameter of 350 A. The porosity was 55.9%; pore volume, 0.77 cc/g; and the surface area was about 75 $m^2/g$.

The BMBD solution was prepared by dissolving 5 mg of BMBD in 5 ml of a 75% acetone-25% water solution. The glucose isomerase preparation was in powder form and said to have an activity of 444 International Glucose Isomerase Units (IGIU) per gram.

The carrier was treated by placing 2 grams of the porous alumina-silica particles in a 30 ml test tube and adding 5 ml of the BMBD solution at room temperature. The tube was stoppered and placed in a cold room at 9°C and reacted with occasional hand shaking for 1½ hours. The excess unreacted solution was then decanted and the treated carrier was extracted with 15 ml of acetone for 15 minutes at 9°C. The carrier was then placed on filter paper in a Buchner funnel and washed with 100 ml acetone and air dried.

The glucose isomerase solution was prepared by adding 3.5 g of the enzyme powder preparation to a beaker and adding 20 ml of an aqueous 0.1 M magnesium acetate solution, pH 6.5. The mixture was stirred on a magnetic stirrer at room temperature for 25 minutes and then filtered through filter paper and the residue on the paper was washed with two 5 ml aliquots of 0.1 M magnesium acetate followed by 10 ml of 0.5 M $NaHCO_3$ followed by 3 ml of 0.1 M magnesium acetate, all of which were added to the enzyme solution. The final volume of the combined filtrate and washes was 35 ml, the pH of the solution was 8.2, and the activity was 47.4 IGIU per ml.

Ten ml of the above enzyme solution, precooled to 5°C, was added to 500 mg of the treated carrier in a 15 ml test tube and shaken in a 5°C bath for 4¼ hours. The tube was then removed from the bath and allowed to stand at room temperature for 1½ hours, after which the unreacted solution was decanted and the composite was transferred to a fritted glass funnel with distilled water where it was washed exhaustively with distilled water.

The immobilized glucose isomerase composite was then repetitively assayed with a 36% glucose solution containing 0.005 molar $Mg^{++}$ and 0.001 molar $Co^{++}$ (as chloride salts) at 60°C, pH 6.9 with storage in water at room temperature between assays. The results of the periodic assays, calculated to activities in IGIU per gram of composite, are shown in Table IV.

TABLE IV

| Assay Day | IGIU/g |
|---|---|
| 1 | 70.4 |
| 2 | 55.4 |
| 3 | 50.2 |
| 4 | 43.8 |
| 7 | 51.4 |
| 9 | 52.4 |
| 10 | 48.8 |
| 22 | 41.6 |
| 24 | 47.8 |
| 35 | 45.4 |
| 43 | 43.6 |
| 45 | 36.2 |
| 57 | 36.0 |

EXAMPLE V

Urease Coupled to Porous $SiO_2$ Particles

In this example, the porous inorganic carrier was the porous silica particles generally similar to those used in Example I, but the particle size was 25–60 mesh. The average pore diameter was 510 A, minimum pore diameter was 350 A, and maximum pore diameter was 680 A. The porosity was 65.3%, surface area was 50 m²/g and the pore volume was 0.8. The BMBD solution consisted of 2 mg BMBD dissolved to 10 ml with 0.1 M NaHSO$_3$. The urease solution was prepared by dissolving 1 gram of a crude urease preparation (Nutritional Biochemical Co.), having an activity of 400 Sumner Units/gram, in 100 ml of water and filtering the dispersion through a Watman No. 3 filter paper on a funnel.

The porous silica particles were treated by reacting 500 mg of the carrier with 10 ml of the BMBD solution at 22°C in a shaking water bath for 1¼ hours. The reaction solution was then decanted and 25 ml of distilled water was added to the particles and the mixture was shaken in the 22°C bath for 15 minutes. The above washing procedure was repeated one more time, after which the wash water was decanted and 20 ml of the urease solution was added and the mixture shaken in the 22°C bath for 4 hours. The enzyme solution was then decanted and the composite was washed with a 25 ml portion of distilled water in the 22°C shaking bath for 15 minutes followed by the same washing technique using 25 ml of 0.5 M NaCl solution. The NaCl solution was decanted and 20 ml of 1 M urea solution was added to the composite and the mixture was shaken in the 22°C bath for 15 minutes, after which the urea solution was decanted and the immobilized urease composite was transferred to a stop cock column with water for storage and assays. The composite sample was assayed repetitively via differential conductivity measurements with 1M urea in the column at room temperature. Between assays, the enzyme composite was stored in the column under water at room temperature. The assay results, calculated to Sumner Units (S.U.) per gram are shown in Table V.

TABLE V

| Assay Day | S.U./g |
|---|---|
| 1 | 5.02 |
| 2 | 3.82 |
| 5 | 1.80 |
| 7 | 1.14 |
| 12 | 0.36 |

The above examples indicate that a variety of enzymes can be coupled through a BMBD residue and still yield an immobilized enzyme composite demonstrating stability and relatively long half lives. Inasmuch as the above disclosures can be readily modified by those skilled in the art, it is intended that the above examples should be construed as illustrative and that the scope of the disclosed invention be limited only by the appended claims.

I claim:

1. A method of preparing an immobilized enzyme composite which comprises the steps of (1) reacting an essentially waterinsoluble inorganic carrier with a solution of 4,4'-bi(2-methoxybenzenediazonium chloride) to form surface diazo groups on the carrier, the carrier being porous and having an average pore diameter at least as large as the larger of the enzyme or its substrate but less than about 1000A, the carrier consisting of particles having an average particle size between about 4 to 200 mesh, U.S. Standard Sieve, and selected from the group consisting of porous glass, porous alumina, porous silica, and porous mixtures of alumina and silica; (2) removing the surface-treated carrier from the reaction solution; and (3) then reacting the treated carrier with an aqueous enzyme solution to chemically couple enzymes to the carrier through the surface diazo groups.

2. The method of claim 1 wherein the enzyme of the aqueous enzyme solution is alkaline *Bacillus subtilis* protease and the carrier consists of porous silica particles.

3. The method of claim 1 wherein the enzyme of the enzyme solution consists of papain and the carrier consists of porous glass particles.

4. The method of claim 1 wherein the enzyme of the enzyme solution is glucose isomerase and the carrier consists of an agglomerated mixture of silica and alumina particles.

5. The method of claim 1 wherein the enzyme of the enzyme solution is urease and the carrier consists of silica particles.

6. An immobilized enzyme composite comprising an enzyme coupled chemically to porous inorganic carriers in accordance with the method of claim 1.

* * * * *